United States Patent [19]

Fain et al.

[11] Patent Number: 4,901,581
[45] Date of Patent: Feb. 20, 1990

[54] METHOD AND APPARATUS FOR TESTING STRETCH FILM

[75] Inventors: John Fain; Patrick R. Lancaster, IV, both of Louisville, Ky.

[73] Assignee: Lantech, Inc., Louisville, Ky.

[21] Appl. No.: 302,986

[22] Filed: Jan. 30, 1989

[51] Int. Cl.$^4$ ............................ G01N 3/00; G01L 5/04
[52] U.S. Cl. ......................................... 73/795; 73/159
[58] Field of Search ................ 73/158, 159, 785, 788, 73/789, 794, 795, 826, 831, 833–835, 838, 852, 853, 856, 828

[56] References Cited

U.S. PATENT DOCUMENTS

| | | | |
|---|---|---|---|
| 2,709,915 | 6/1955 | Lonti | 73/853 |
| 2,966,792 | 1/1961 | Pieri | 73/159 |
| 3,460,379 | 8/1969 | Webb | 73/831 |
| 3,724,266 | 4/1973 | Beckstrom | 73/831 |
| 3,835,697 | 9/1974 | Schneider et al. | 73/159 |
| 3,877,302 | 4/1975 | Miller | 73/159 |

FOREIGN PATENT DOCUMENTS

| | | | |
|---|---|---|---|
| 1265515 | 10/1986 | U.S.S.R. | 73/158 |

OTHER PUBLICATIONS

Dunn, "Testing Device", IBM Technical Disclosure Bulletin, vol. 15, No. 8, Jan. 1973, p. 2501.

Primary Examiner—Robert R. Raevis
Attorney, Agent, or Firm—Finnegan, Henderson, Farabow, Garrett & Dunner

[57] ABSTRACT

A method and apparatus for testing the properties of stretch film include collapsing a web of stretch film into a rope, anchoring the rope web at two locations and stretching an intermediate portion of the rope web a first distance in a first direction between the locations where it is anchored. The intermediate portion of the stretched roped web is displaced a second distance along a second direction transverse to the first direction and relative to the locations where it is anchored, and the tension force in the stretched roped web is measured when it is displaced the second distance. Alternatively, peripheral portions of a sheet of stretch film are secured and a central portion of the sheet of stretch film is engaged and deformed a third distance in the second direction.

19 Claims, 5 Drawing Sheets

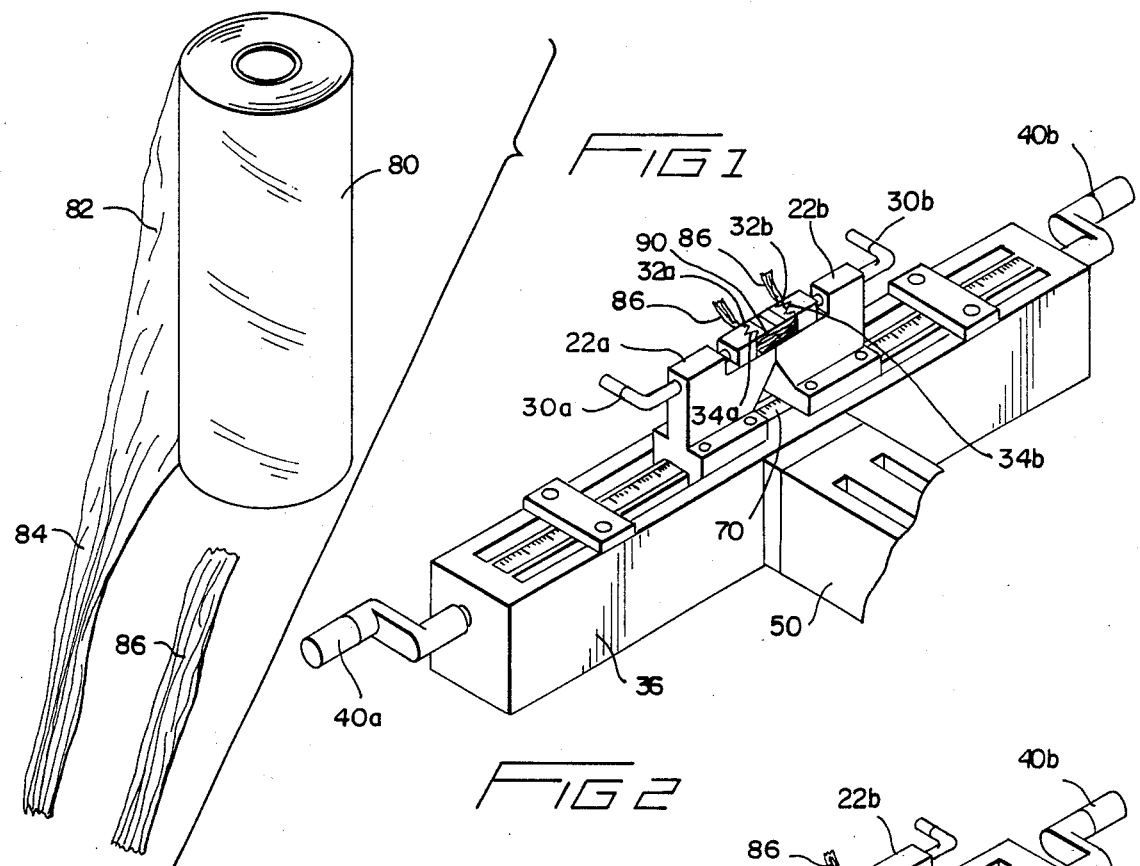

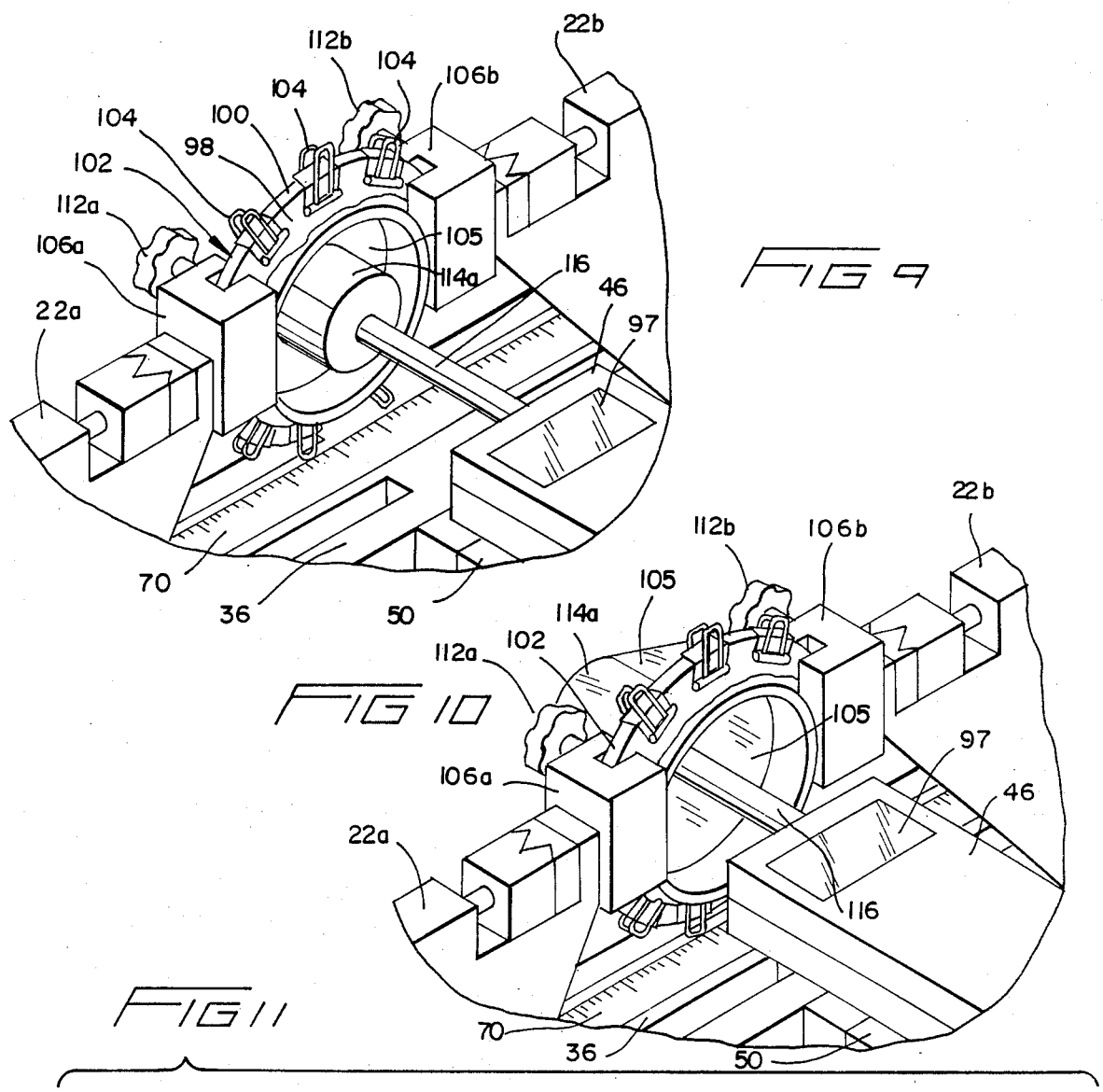
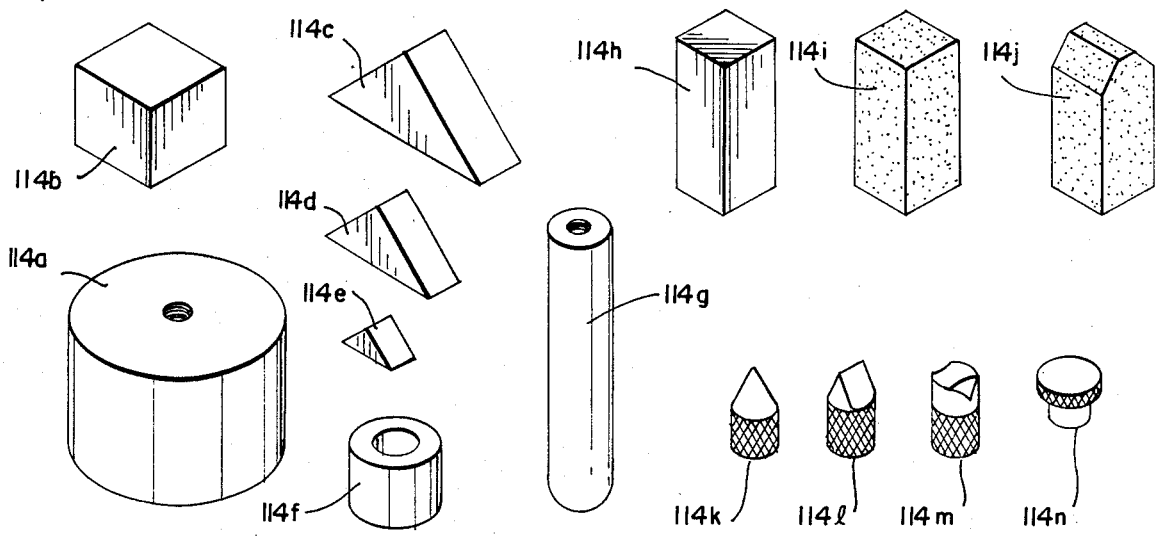

METHOD AND APPARATUS FOR TESTING STRETCH FILM

BACKGROUND OF THE INVENTION

The present invention relates to a method and apparatus for testing stretch film.

During the past two decades, considerable developments have been made in the field of wrapping a load with a stretched web of film to package the load. Most noteably, the film web dispenser used in stretch wrapping operations has developed to the extent that it contains a series of rollers which defines a path through which the film web passes so that it can be prestretched prior to being dispensed on the load. Such stretch wrapping apparatus is disclosed, by way of example, in U.S. Pat. Nos. 4,302,920 and 4,418,510 to Lancaster et al., and assigned to Lantech, Inc. These patents are incorporated herein by reference.

With the advent of prestretch, there has been significant confusion of film users and buyers with film manufacturers specifications and sales claims for their films. The use of traditional laboratory film test information has added to the confusion since the properties reported are not suitable for comparing film qualities to determine the best value for shipping unit loads.

Most marketing energy has been concentrated on "stretch-ability," that is, how far the film will stretch on a particular load with a particular type of stretching or prestretching device. Stretchability largely determines the yield of a particular film and thus the cost to wrap a given load with a given number of unit wrap revolutions. Stretchability is measurable on a load by printing "X's" at known intervals, such as every ten inches, on the film supply roll and then measuring the interval after prestretch and wrapping to calculate the actual increase in the film length. Stretchability tests have been done to stretch film and measure percent stretch at film rupture.

The second and often overlooked film characteristic is "relative restretch force." The most important function of stretch film is to hold together as a unit a group of products such as cartons, bags, or bottles. The ability of a film wrap to hold the unit together is largely a function of the unitizing or banding force available to maintain the individual subunit components of the unit together during shipment or material handling.

When an individual subunit shifts during transit of the load and moves away from the unit, the film is restretched so that the film near the shifting subunit is stretched further than it was stretched during the original wrapping process. It is desirable that the force exerted on the load by the film during restretch is as high as possible because a higher force would stop the momentum of subunit at the earliest possible time and produce the best results in terms of holding the package as a unit. A film exhibiting twice as much restretch force as another film may well require only half as many revolutions of film to be applied for equivalent shipment security. Such a film would reduce the cost for unitizing a load substantially.

The force exerted by the film on a shifting subunit of a load is called restretch force. It is further defined as the force required to substantially extend film which had previously been stretched around a load. The force required for initial restretching is substantially dependent upon original wrapping force. As the film is restretched further, the force required for restretching becomes closely proportional to ultimate film strength.

Initial restretch force testing was done by instrumenting a simulated load with an extendable corner. After wrapping, the corner was extended outward and the force required was measured with an electronic load cell. Mobil Chemical demonstrated a variation of this concept at the 1988 PMMI trade show using an extendable pad mounted in the side of simulated unit load. Relative restretch force also has been crudely measured on a load by inserting a rod or pad through a horizontal slit and then pulling a predetermined distance with an electronic or spring scale.

The third important stretch film characteristic is "moldability." This is the ability of the film to conform over irregular objects. Moldability is a critical characteristic when wrapping irregular shaped units such as "order picking" loads of many different sized and shaped products. It also may be critical when the load does not fit the pallet and the film will be required to extend around the sharp corners of pallet deck boards and stringers. This characteristic has been measured and compared by successively wrapping films on a simulated load with several levels of protrusions to determine the failure mode. It also is relatively determinable by repetitively wrapping a certain load with several films and observing failures. Film moldability is dependent upon the balance of several traditionally measured film characteristics including elastic modules, puncture and tear properties.

The first two characteristics, stretchability and restretch force, in combination with film cost are the most important elements in determining relative unitizing cost when comparing two or more stretch film candidates. The third characteristic "moldability" is added to the first two when the unit to be wrapped has a very irregular shape or when it does not fit the pallet.

The need for cumbersome laboratory type equipment such as instron equipment, instrumented loads, or crude field observations to determine these film characteristics has made it very difficult for film users to make an intelligent selection of a film that will insure an optimum film cost per load effectively shipped and handled to its ultimate destination.

Accordingly, it is an object of the present invention to provide a portable test apparatus easily transported and demonstrated on a desk top and a process for using the test apparatus to compare the most important unitizing characteristics of several stretch films to determine the one most likely to unitize a particular product securely through shipment and material handling at the lowest possible film cost.

Additional objects and advantages of the invention will be set forth in the description which follows, and in part will be obvious from the description, or maybe learned by practice of the invention. The objects and advantages of the invention may be realized and obtained by means of the instrumentalities and combinations particularly pointed out in the appended claims.

SUMMARY OF THE INVENTION

To achieve the foregoing objects and in accordance with the purposes of the invention as embodied and broadly described herein, there is provided a method for testing the properties of stretch film. The method includes collapsing a web of stretch film into a rope, anchoring the roped web at two locations and stretching an intermediate portion of the roped web a first distance in a first direction between the locations where it is anchored. The intermediate portion of the stretched rope web is displaced a second predetermined distance along a second direction transverse to the first direction and relative to the locations where it is anchored, and the tension force in the stretched roped web is measured when it is displaced the second distance.

An apparatus is provided for testing the properties of stretch film. The apparatus includes first and second means for anchoring a rope web of stretch film at two locations and means for moving the first and second anchor means away from each other for stretching an intermediate portion of the roped web the first distance in a first direction between the first and second anchor means. Means are provided for engaging and displacing the intermediate portion of the stretched roped web a second distance along a second direction transverse to the first direction and relative to the anchor means, and for measuring the tension force in the stretched roped web when it is displaced in the second direction.

It is preferable that the apparatus also includes means for securing peripheral portions of a sheet of stretch film and for exposing a central portion of the sheet of stretch film for deformation in the second direction, and that the means for engaging and displacing the intermediate portion of the roped web alternatively engages and displaces the central portion of the sheet of stretch film relative to the peripheral portion of the sheet of stretch film a third distance in the second direction. It is also preferable that the means for measuring the tension force in the stretched roped web when it is displaced in the second direction alternatively measures the tension force in the sheet of stretch film when it is displaced in the second direction.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 is a perspective view of a roll of stretch film which has been collapsed into a rope and severed to form a roped segment in accordance with the teachings of the present invention.

FIG. 2 is a partial perspective view of the roped web segment of FIG. 1 anchored in an apparatus for testing stretch film at the beginning of a test for the stretchability or relative restretch of the stretch film according to the teachings of the present invention.

FIG. 3 is a partial perspective view of the apparatus shown in FIG. 2 subsequent to performing a test for the stretchability of the stretch film.

FIG. 9 is a partial perspective view of the apparatus shown in FIG. 2 with additional apparatus at the beginning of a test for the moldability of stretch film.

FIG. 10 is a partial perspective view of the apparatus shown in FIG. 9 at the completion the test for moldability of stretch film.

FIG. 11 is a perspective view of various elements which can be used in conducting the moldability test shown in FIGS. 9 and 10.

DESCRIPTION OF THE PREFERRED EMBODIMENT

Reference will now be made in detail to the present preferred embodiment of the invention as illustrated in the accompanying drawings.

Figure 6:
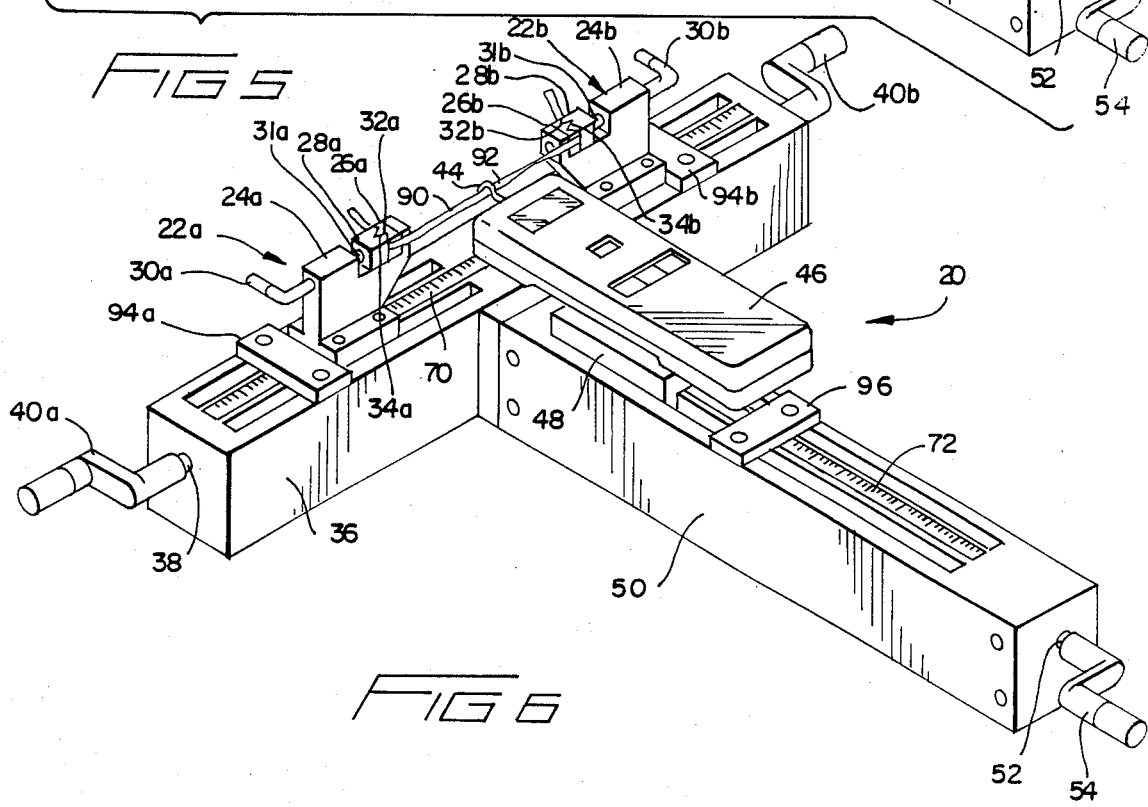
FIG. 6 is a perspective view of the apparatus shown in FIG. 2, in its assembled state during a test for relative restretch of the stretch film, prior to restretching the stretch film.

In accordance with the present invention there is provided an apparatus for testing the properties of stretch film. As shown in FIG. 6, the apparatus is generally designated by the numeral 20.

In accordance with the present invention, there is provided first and second means for anchoring a roped web of stretch film at two locations. As shown in FIG. 6, the first and second anchoring means respectively include first vice 22a and second vice 22b. First vice 22a includes a T-shaped body portion 24a, a fixed jaw portion 26a which is attached to the T-shape body portion 24a, and a movable jaw portion 28a which can be advanced toward and retracted from fixed jaw portion 26a by handle 30a which engages movable jaw portion 28a with a screw 31a. It is preferable that the opposed portions of the fixed and movable jaws 26a and 28a include complementary zig-zag gripping surfaces 32a and 34a for securing the roped segment of stretch film. Second vice 22b is similar in design to first vice 22a. The components of second vice 22b correspond to those discussed with respect to first vice 22a are designated by identical numerals with a "b" suffix.

In accordance with the present invention there is provided means for moving the first and second anchor means away from each other for stretching an intermediate portion of the roped web a first distance in a first direction between the first and second anchor means.

As shown in FIG. 6, the moving means include an elongated rectangular aluminum support frame 36, a screw 38 running longitudinally through the center of frame 36, and crank handles 40a and 40b attached to the ends of screw 38 which extend from frame 36. First and second vices 22a and 22b are attached to screw 38 by ball screw nuts (not shown). The portions of screw 38 which engage respective ball screw nuts are inclined in opposite directions so that when handles 40a and 40b are used to turn screw 38, screw 38 acts as a means for simultaneously moving the first and second anchoring means apart, when turned in one direction, and together, when turned in the other direction.

According to the present invention, there is provided means for engaging and displacing an intermediate portion of the stretched roped web at a second distance along a second direction transverse to the first direction and relative to the anchor means, and means for measuring the tension force in the stretched roped web when it is displaced in the second direction.

As shown in FIG. 6, the means for engaging the roped web includes a hook 44 for engaging an intermediate portion of the roped web of stretch film. The measuring means includes an electronic load cell 46 (such as the Ametek Model Accuforce Cadet Digital Force Gauge, manufactured by Ametek of Largo, Fla.) to which hook 44 is releasably attached and which measures the force applied to hook 44. Load cell 46 is mounted to an I shaped bracket 48 which rides on an elongated rectangle aluminum support frame 50. A screw 52 runs the length of support frame 50 and is attached at one end to crank handle 54. Bracket 48 is attached to screw 52 by a ball nut (not shown).

Figure 4:
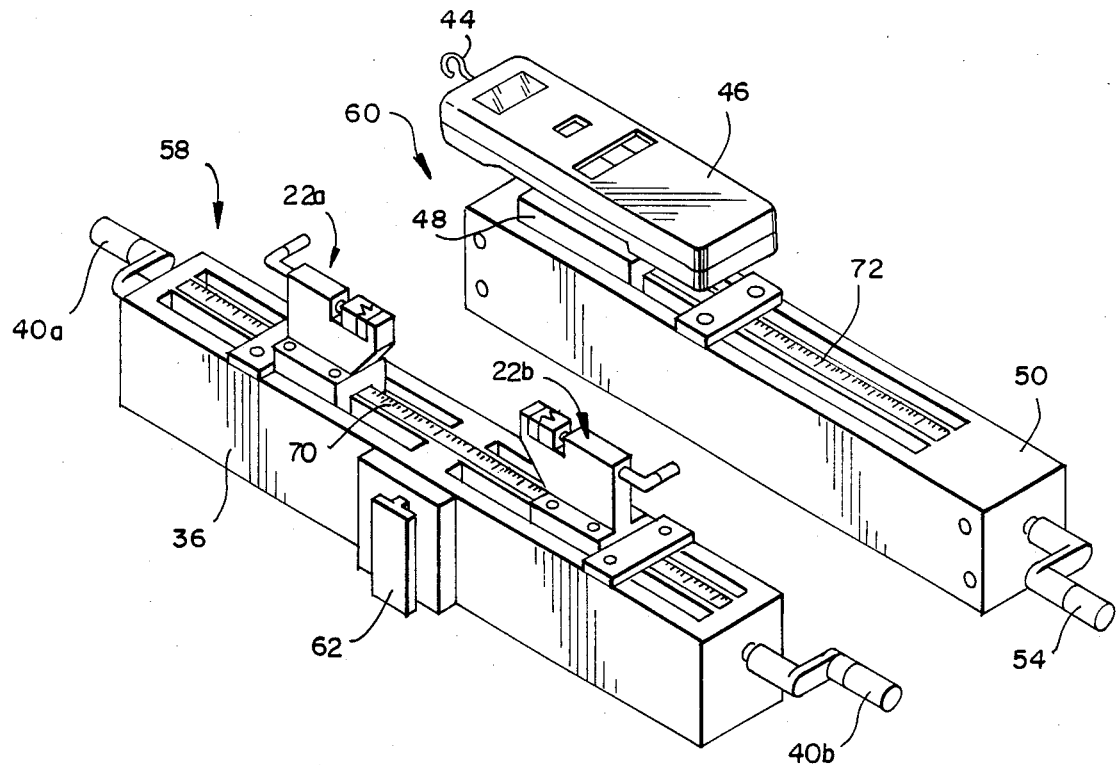
FIG. 4 is a perspective view of the apparatus shown in FIG. 2 disassembled and oriented for compact storage.
Figure 5:
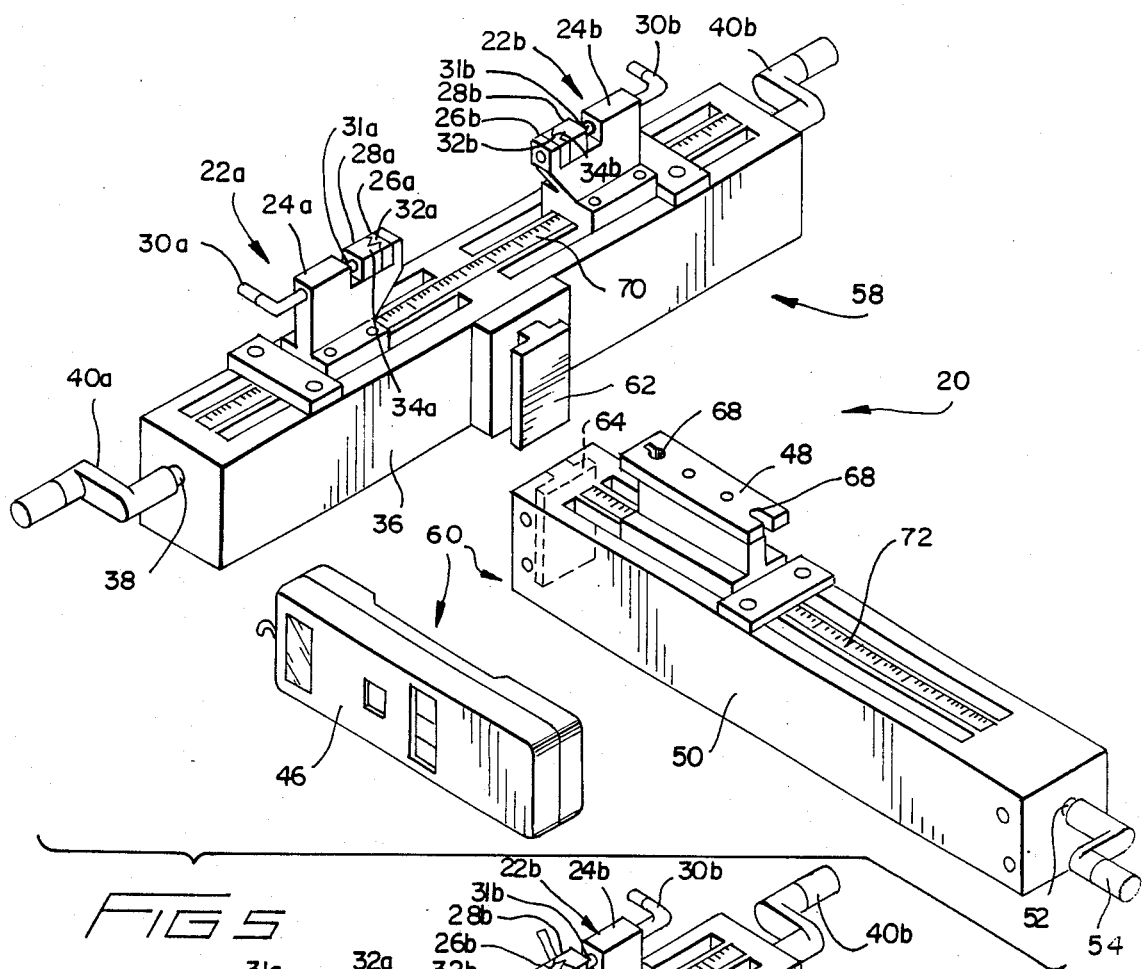
FIG. 5 is a perspective view of the apparatus shown in FIG. 2, disassembled and oriented for assembly.

As shown in FIGS. 4 and 5, the anchoring and moving means, which includes the first and second vices 22a and 22b and support frame 36 with crank handles 40a and 40b, is a first subassembly 58. The engaging, displacing and measuring means, which include hook 44, load cell 46, bracket 48, support frame 50 and crank handle 54 is a second subassembly 60 of the apparatus. First and second subassemblies 58 and 60 of the apparatus are releasably secured when in use and separable for storage. Tongue portion 62 of the first subassembly 58 fits in a complimentary groove portion 64 of second subassembly 60 to releasably connect the two subassemblies together. The first and second subassemblies 58 and 60 are slender members, each having a longitudinal extent which is substantially greater than its height and width. When secured together for use, the subassemblies form a T with one end of second assembly 60 adjoining a central portion of first subassembly 58.

It is preferable that the tension measuring means is assembled to the engaging and displacing means shown in FIG. 5. Load cell 46 has tabs (not shown) on its lower surface which fit into holes 68 of bracket 48, shown in FIG. 5.

It is preferable that the first and second subassemblies include means for measuring distance in each of the first and second directions. As shown in FIGS. 5 and 6, the top surface of support frame 36 of first subassembly 58 has a scale 70 in inches and fractions of inches running in the first direction along its length. Similarly, the top surface of support frame 50 of second subassembly 60 has a scale 72 in inches and fractions of inches extending in the second direction along its length.

Figure 7:
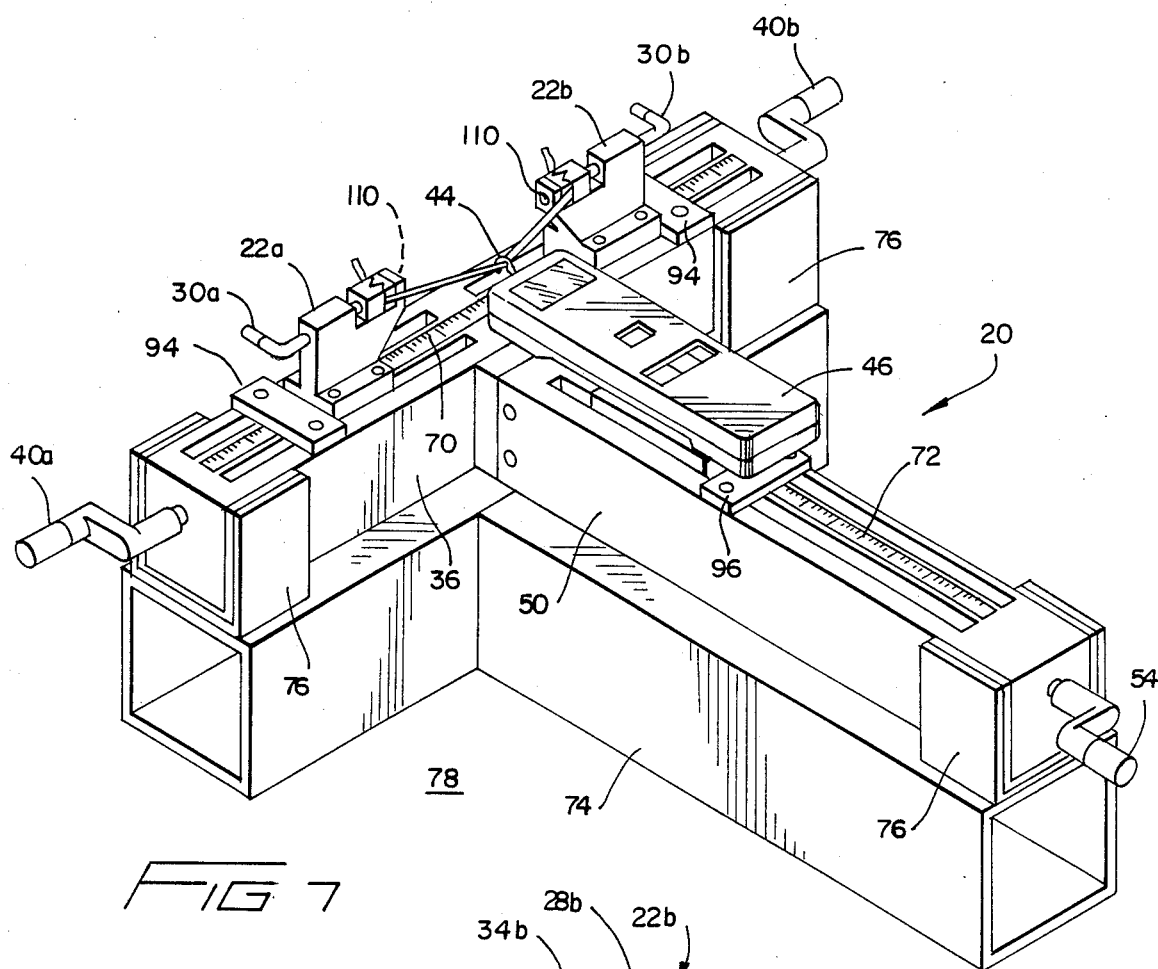
FIG. 7 is a perspective view of the apparatus shown in FIG. 6 on its support stand during a test for relative restretch of the stretch film, after partially restretching the stretch film.

As shown in FIG. 7, first and second subassemblies 58 and 60, when assembled, are mounted on a T shaped support frame 74 having flanges 76 to hold first and second subassemblies 58 and 60 in place. Frame 74 also allows for clearance between a desk top 78 on which the support frame 74 is located and crank handles 40a, 40b and 54.

As shown in the sequence of FIGS. 5, 6 and 7, the test apparatus is assembled by joining first and second subassemblies 58 and 60 together and mounting them between flanges 76 in T shaped frame 74. The device is capable of three different types of film tests in this arrangement, relative stretchability, relative restretch force, and relative moldability.

According to the present invention it is preferable to provide means for securing peripheral portions of a sheet of stretch film and for exposing a central portion of the sheet of stretch film for deformation in the second direction transverse to the first direction. In addition, it is preferable that the means for engaging and displacing the intermediate portion of the roped web alternatively engages and dispaces the central portion of the sheet of stretch film relative to the peripheral portion of the sheet of stretch film a third distance in the second direction. Also, the means for measuring the tension force in the stretched roped web when it is displaced in the second direction, alternatively measures the tension force in the sheet of stretch film when it is displaced in the second direction.

As shown in FIG. 9, the means for securing and exposing a sheet of stretch film includes a metal annulus 102 having an L shaped cross section with radially extending flange 100. The means also includes spring clips 104 which secure peripheral portions of an unroped sheet 98 of stretch film to flange 100 while exposing a central portion 105 of the sheet 98, Additionally, the means includes slotted clamps 106a and 106b which secure the annulus to first and second vices 22a and 22b through the use of pins (not shown) which are insertable into holes 110 (shown in FIGS. 7 and 8.) Knobs 112a and 112b turn respective screws to clamp annulus 102 in place on slotted clamps 106a and 106b.

During the test for relative moldability the means for securing and exposing is located so that the central portion of the sheet sample is aligned with the means for engaging and displacing. Accordingly, during that test for moldability, the means for engaging and displacing, which was used to engage and displace the intermediate portion of the roped web in the second direction during the restretch force test, is alternatively used to engage and displace the central portion of the sheet sample in the second direction during the moldability test. Similarly, the means for measuring the tension force in the stretched roped web when it is displaced in the second direction during the restretch force test, alternatively measures the tension force in the sheet of stretch film when it is displaced in the second direction during the moldability test.

1. Relative Stretchability Test

As shown in FIG. 1, a roll 80 of stretch film 82 is partially unwound and stretch film 82 is collapsed to a rope shape to form a roped web 84 of stretch film. Roped web 84 is cut into segments 86 which are approximately 6 inches long, through the use of scissors.

As shown in FIG. 2, the tightly roped segment 86 is pulled tight by hand and anchored at two locations, namely between gripping surfaces 32a, 34a of first vice 22a and gripping surfaces 32b, 34b of second vice 22b. At the time roped web 84 is anchored, first and second vices 22a and 22b are positioned close together to form a sample 90 from an intermediate portion of segment 86. For this test, it is preferable that sample 90 is one inch long as measured between gripping surfaces 32a, 34a and 32b, 34b.

First and second vices 22a and 22b are separated at a constant speed by turning either crank handle 40a or 40b. It is possible to obtain good results by using an electronic metronome device for timing. Crank handles 40a or 40b are turned until film sample 90 breaks, as shown in FIG. 3. The distance between first and second vices 22a and 22b is measured at this point using scale 70. Relative stretchability can be expressed in terms of percentage by using the following formula (inches at break minus 1 times 100) when the sample is originally set at a one inch sample length.

2. Relative Restretch Force Test

According to the present invention, a web of stretch film is collapsed into a rope and anchored at two locations. An intermediate portion of the roped web is stretched between the locations where it is anchored from a first length to a second length which is greater than the first length. The intermediate portion of the roped web is then stretched to a third length which is greater than the second length, and the tension force in the stretched rope web is measured when it is stretched to the third length. It is preferable that the roped web is stretched a first distance in a first direction between the locations where it is anchored, and then displaced a second distance along a second direction tranverse to the first direction and relative to the locations where it is anchored.

As discussed in more detail above, a segment 86 of roped web 84 is made as shown in FIG. 1, and clamped in vices 22a and 22b to form sample 90 as shown in FIG. 2. For this test it is preferable that sample 90 is two inches long between gripping surfaces 32a, 34a and gripping surfaces 32b, 34b in an unstretched state at the beginning of this test.

First and second vices 22a and 22b are then separated to precisely stretch sample 90 to a length of six inches as shown in FIG. 6 by rotating crank handles 42a or 42b. Stops 94a and 94b can be provided on support frame 36 to ensure accuracy in this portion of the test. As shown in FIG. 6, hook 44 on electronic load cell 46 is positioned to engage the intermediate portion of sample 90 at its midpoint 92. Sample 90 is then restretched by displacing the intermediate portion of the stretched roped web sample 90 a second predetermined distance along a second direction transverse and perpendicular to the direction in which it is was first stretched, by rotating crank handle 54 and moving hook 44 and load cell 46 through the position shown in FIG. 7 to the position shown in FIG. 8.

Figure 8:
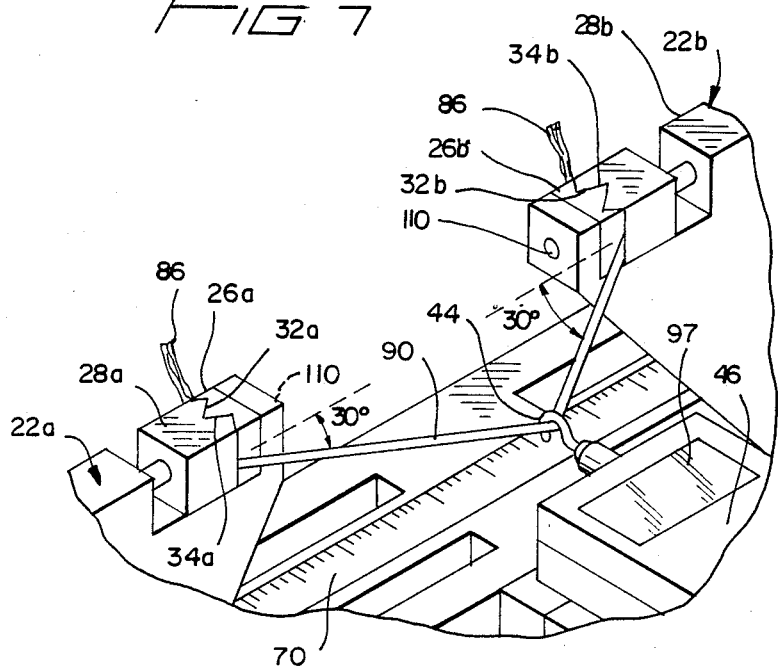
FIG. 8 is a partial perspective view of a portion of the apparatus shown in FIG. 6 at the completion of a relative restretch film test.

During the restretching step, it is preferable to displace the stretched roped web over an angle of 30° so that the restretched film web forms a 30° angle with the orientation of the original sample line as shown in FIG. 8. Stop 96 can be provided on support frame 50 to ensure accuracy in this portion of the test. The maximum force is noted from a readout 97 on load cell 46. This becomes the relative restretch force. The timing of the stretch and restretch phases of this test has some minimal inpact and should be done consistently. Effective tests were accomplished by pausing for about one minute between completing the stretching step and beginning the restretching step to allow for stretch relaxation to occur.

The initial pulling of the stretching step simulates a nominal 200% prestretch. This could be varied according to the general range of stretchability intended. The second pulling during the restretch steps simulates the forces available to stop a subunit from escaping the unitizing forces of the film. Such forces occur during an abrupt turn or stopping of the units during transport which causes the subunits to shift.

A restretch displacement of 30° was chosen because it allows the force read on the load cell to accurately relate to the force on the film without any correction factor.

Although it is preferable to perform the restretch test by stretching an intermediate portion of the roped web in a first direction between the locations where it is anchored, and then displacing the intermediate portion of the stretched rope web along a second direction transverse to the first direction, it is possible to perform the test when the second direction is not transverse to the first direction. For example, the step of stretching the rope web from a first length to a second length can be accomplished by stretching the roped web between the positions shown in FIGS. 6 and 7, while the step of continuing to stretch the roped web can be accomplished by the steps shown in the sequence between FIGS. 7 and 8, so that the stretching and restretching steps are performed in the same direction rather than in directions that are transverse to each other.

The restretch test can be verified by prestretching film 200% and then wrapping on a load at the same stretch level and using an X tester as described above. After placing a horizontal slot in the film, a rod of a nominal 12 inch length is placed into the slit and rotated into a vertical position. After attaching a spring scale or electronic scale to the rod, the rod is pulled away from the plane of the side of the load to form a 30° angle from the side of the load. The relative forces have been found to correlate with the results of the relative restretch force test described above.

3. Relative Moldability Test

As shown in FIG. 9, an unroped sample 98 of a stretch film sheet is secured onto a flange 100 of an annulus 102 with clips 104 to form an exposed firm central drum head portion 105 over annulus 102. Slotted clamps 106a and 106b are mounted on first and second vices 22a and 22b through the use of pins (not shown) which fit into corresponding holes 110 on the inwardly facing surfaces of fixed jaw portions 26a and 26b of first and second vices 22a and 22b. Knobs 112a and 112b turn respective screws to clamp annulus 102 in place on slotted clamps 106a and 106b.

A probe is chosen, for example from the selection of different shaped probes 114a-114n shown in FIG. 11 as a means for engaging the sheet of stretch film. Such probes simulate the type of protrusion found in the types of loads to be wrapped. As shown in FIG. 9, a cylindrical probe 114a is mounted on a shaft 116 which is mounted on load cell 46 in an interchangeable fashion in place of hook 44. Crank handle 54 is rotated to advance the probe 114a in the second direction from the position shown in FIG. 9 where the probe first engages film sample 98 to the position shown in FIG. 10 when the probe is pushed through and ruptures the film sample. The maximum force at the time of rupture is noted from readout 97 on load cell 46 and the depth of the protrusion is measured by calculating the distance the probe is advanced against scale 72. The depth of protrusion is the most important indicator of relative moldability.

Additional advantages and modifications will readily occur to those skilled in the art. The invention in its broader aspects is, therefore not limited to the specific details, representative apparatus and illustrative examples shown and described. Accordingly, departures may be made from such details without departing from the spirit or scope of the general inventive concept as defined by the appended claims and their equivalents.

What is claimed is:

1. A method for testing the properties of stretch film comprising:
    collapsing a web of stretch film into a rope;
    anchoring the roped web at two locations;
    stretching an intermediate portion of the roped web a first distance in a first direction between the locations where it is anchored;
    displacing the intermediate portion of the stretched roped web a second distance along a second direction transverse to the first direction and relative to the locations where it is anchored; and measuring the tension force in the stretched roped web when it is displaced the second distance.

2. The method of claim 1 wherein the displacing step includes displacing the intermediate portion of the stretched roped web with a force measuring device.

3. The method of claim 2 wherein the second direction is perpendicular to the first direction.

4. The method of claim 3 wherein the force measuring device engages the stretched roped web at a central location equidistant from the locations where the stretched roped web is anchored.

5. The method of claim 4 wherein the displacing step displaces the stretched roped film to an angle of 30° from the position of the stretched roped film before the displacing step.

6. The method of claim 1 wherein the roped web between the two anchor locations is stretched from a length of two inches before the stretching step to a length of six inches after the stretching step.

7. An apparatus for testing the properties of stretch film comprising:
   first and second means for anchoring a roped web of stretch film at two locations;
   means for moving the first and second anchor means away from each other for stretching an intermediate portion of the roped web a first distance in a first direction between the first and second anchor means;
   means for engaging and displacing the intermediate portion of the roped web a second distance along a second direction transverse to the first direction and relative to the anchor means; and
   means for measuring the tension force in the stretched roped web when it is displaced in the second direction.

8. The apparatus of claim 7 wherein the tension measuring means is coupled to the engaging and displacing means.

9. The apparatus of claim 7 wherein the means for anchoring and moving are a first subassembly, and the means for engaging, displacing and measuring are a second subassembly which is releasably secured to the first subassembly when in use and separable from the first subassembly for storage.

10. The apparatus of claim 9 wherein the first and second subassemblies are each slender members, and when secured together for use form a T with one end of the second subassembly adjoining a central portion of the first subassembly.

11. The apparatus of claim 7 including means for measuring distance in each of the first and second directions.

12. The apparatus of claim 7 wherein each of the anchoring means includes a vice with jaws having complementary zig-zag gripping surfaces.

13. The apparatus of claim 7 wherein the moving means includes screw means for simultaneously moving the first and second anchoring means apart.

14. The apparatus of claim 7 wherein the displacing means includes screw means for advancing and retracting the engaging means.

15. The apparatus of claim 7 including means for measuring distance in each of the first and second directions, and wherein the tension measuring means is assembled to the engaging and displacing means, the moving means include screw means for moving the first and second anchoring means apart, and the displacing means includes second screw means for advancing and retracting the engaging means.

16. The apparatus of claim 15 wherein the means for anchoring and moving are a first subassembly, and the means for engaging, displacing and measuring are a second subassembly which is releasably secured to the first subassembly when in use and separable from the first subassembly for storage.

17. The apparatus of claim 16 wherein the first and second subassemblies are each slender members, and when secured together for use form a T with one end of the second adjoining a central portion of the first subassembly.

18. The apparatus of claim 17 wherein each of the anchoring means includes a vice with jaws having complimentary zig zag gripping surfaces.

19. An apparatus for alternatively testing the relative stretchability, relative restretch force and relative moldability of stretch film comprising:
   first and second means for anchoring a roped web of stretch film at two locations;
   means for moving the first and second anchor means away from each other for stretching an intermediate portion of the roped web a first distance in a first direction between the first and second anchor means;
   means for securing peripheral portions of a sheet of stretch film and for exposing a central portion of the sheet of stretch film for deformation in a second direction transverse to the first direction;
   means for displacing the intermediate portion of the roped web a second distance along the second direction and relative to the anchor means, and for alternatively displacing the central portion of the sheet of stretch film relative to the peripheral portion of the sheet of stretch film a third distance in the second direction; and
   means for measuring the tension force in the stretched roped web when it displaced in the second direction, and for alternatively measuring the tension force in the sheet of stretch film when it is displaced in the second direction.

* * * * *

UNITED STATES PATENT AND TRADEMARK OFFICE
CERTIFICATE OF CORRECTION

PATENT NO. : 4,901,581

DATED : February 20, 1990

INVENTOR(S) : John Fain et al.

It is certified that error appears in the above-identified patent and that said Letters Patent is hereby corrected as shown below:

Claim 17, col. 10, line 24: "second adjoining" should be --second subassembly adjoining--.

Signed and Sealed this

Twelfth Day of March, 1991

Attest:

HARRY F. MANBECK, JR.

*Attesting Officer*　　　　　*Commissioner of Patents and Trademarks*